US012778803B2

(12) United States Patent
Hannon et al.

(10) Patent No.: US 12,778,803 B2
(45) Date of Patent: Nov. 3, 2026

(54) CORNEAL MARKER TOOLS FOR OPHTHALMIC PROCEDURES

(71) Applicant: AMO Development, LLC, Irvine, CA (US)

(72) Inventors: Trevor Hannon, Hayward, CA (US); Vyechi Low, San Jose, CA (US); Christina Lagarto, Sunnyvale, CA (US); Jose Garcia, Fremont, CA (US); Hong Fu, Pleasanton, CA (US); Deepali Mehta-Hurt, Newark, CA (US)

(73) Assignee: AMO Development, LLC, Irvine, CA (US)

( * ) Notice: Subject to any disclaimer, the term of this patent is extended or adjusted under 35 U.S.C. 154(b) by 925 days.

(21) Appl. No.: 17/457,411

(22) Filed: Dec. 2, 2021

(65) Prior Publication Data

US 2022/0175582 A1 Jun. 9, 2022

Related U.S. Application Data

(60) Provisional application No. 63/121,200, filed on Dec. 3, 2020.

(51) Int. Cl.
*A61F 9/013* (2006.01)

(52) U.S. Cl.
CPC .................................. *A61F 9/0136* (2013.01)

(58) Field of Classification Search
CPC ............... A61F 9/0136; A61M 35/003; A61M 37/0084; A61B 90/39; A61B 2090/3933; A61B 2090/3937; A61B 2090/395; A61B 2090/3987; B43K 1/003; B43K 1/006; B43K 1/01; B43K 1/015; B43K 1/02; B43K 1/04; B43K 5/00; B43K 5/005;
(Continued)

(56) References Cited

U.S. PATENT DOCUMENTS 5,054,504 A * 10/1991 Winrow ................. A61H 7/003 132/110
5,339,839 A * 8/1994 Forcelledo ............. A45D 24/26 132/114

(Continued)

FOREIGN PATENT DOCUMENTS

GB 2348812 A 10/2000

*Primary Examiner* — Diane D Yabut
*Assistant Examiner* — Christian D Knauss

(57) ABSTRACT

Various corneal marker tools and assemblies are provided for use in ophthalmic procedures to place ink marks on the cornea. One tool assembly includes an applicator containing an ink and a disposable marking tip attachable to the applicator, where ink is injected from the applicator into hollow channels of the marking tip. Another tool assembly includes a reusable handle and a disposable marking tip attachable to the handle. Another tool assembly includes a marker assembled with a cap with an ink pad. Another tool assembly includes a marker tool and a nesting adapter to be used with a patient interface device. Other tools have a one-piece design with a marker head and an handle fixedly joined together. Some tools have pre-inked marking elements, or an embedded light source, or a built-in level indicator, or a ring-shaped marker head, or a leaf spring feature on their marking prongs.

17 Claims, 8 Drawing Sheets

(58) Field of Classification Search
CPC . B43K 5/02; B43K 8/00; B43K 8/003; B43K 8/006; B43K 8/08; B43K 8/022; B43K 8/024; B43K 8/026; B43K 8/028
See application file for complete search history.

(56) References Cited

U.S. PATENT DOCUMENTS

| | | | | |
|---|---|---|---|---|
| 5,913,314 | A * | 6/1999 | Garrett | A45D 19/028 401/268 |
| 6,217,596 | B1 | 4/2001 | Farah | |
| 7,077,146 | B1 * | 7/2006 | Eckerson | A45D 24/28 132/112 |
| 8,491,616 | B2 | 7/2013 | Davis | |
| 9,011,470 | B2 | 4/2015 | Mackool | |
| 9,283,117 | B2 | 3/2016 | Brown | |
| 9,668,920 | B2 | 6/2017 | Akahoshi | |
| 10,004,642 | B1 | 6/2018 | Nallakrishnan et al. | |
| 10,022,271 | B2 | 7/2018 | Brown | |
| 10,201,454 | B2 | 2/2019 | Brown | |
| 2002/0103481 | A1 | 8/2002 | Webb et al. | |
| 2004/0167540 | A1 | 8/2004 | Gerten | |
| 2007/0203504 | A1 | 8/2007 | Denny et al. | |
| 2008/0228210 | A1 | 9/2008 | Davis | |
| 2012/0203239 | A1 | 8/2012 | Vukich et al. | |
| 2012/0209280 | A1 | 8/2012 | Macken | |
| 2012/0245609 | A1 | 9/2012 | Brown | |
| 2013/0035705 | A1 | 2/2013 | Fath et al. | |
| 2013/0060271 | A1 | 3/2013 | Sunalp | |
| 2013/0340781 | A1 * | 12/2013 | Liebel | A45D 24/30 132/110 |
| 2014/0324083 | A1 | 10/2014 | Brown | |
| 2015/0038977 | A1 | 2/2015 | Nallakrishnan | |
| 2015/0150723 | A1 | 6/2015 | Brown | |
| 2015/0366714 | A1 | 12/2015 | Kandavel et al. | |
| 2016/0220012 | A1 * | 8/2016 | Sprosta | A45D 40/04 |
| 2017/0258637 | A1 | 9/2017 | Seiler et al. | |
| 2017/0312134 | A1 | 11/2017 | Brown | |
| 2019/0021909 | A1 | 1/2019 | El-Ayari et al. | |
| 2019/0240072 | A1 | 8/2019 | Brown | |

* cited by examiner

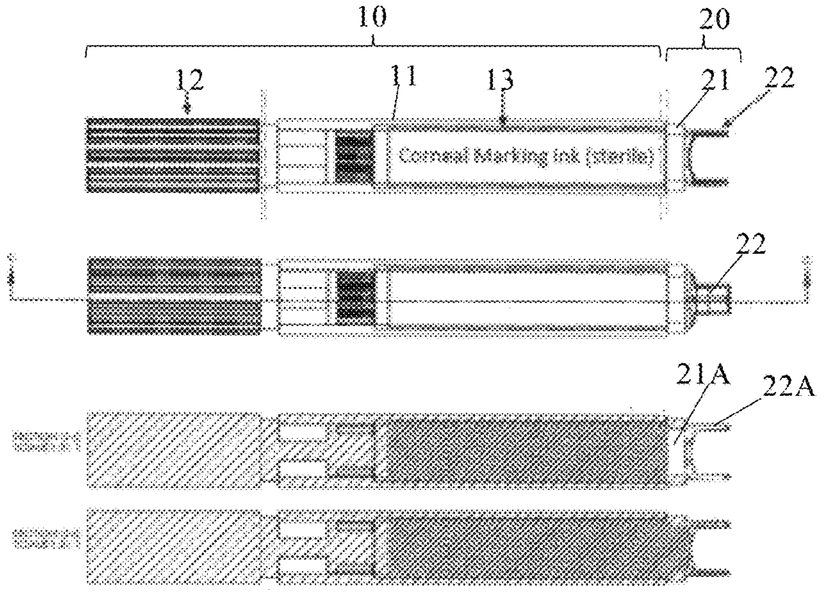
Fig. 1A
Fig. 1B
Fig. 1C
Fig. 1D
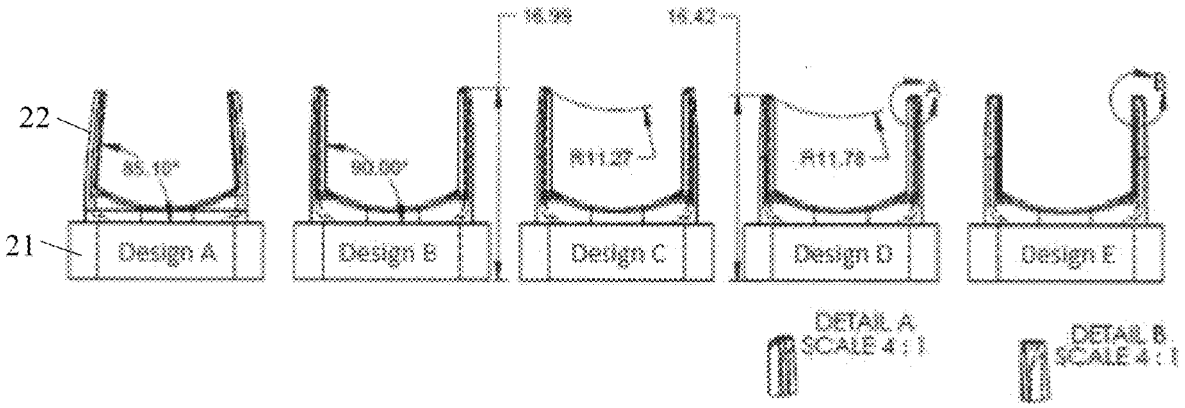
Fig. 2A Fig. 2B Fig. 2C Fig. 2D Fig. 2E

CORNEAL MARKER TOOLS FOR OPHTHALMIC PROCEDURES

CROSS REFERENCE TO RELATED APPLICATIONS

This application claims priority to U.S. Provisional Patent Application No. 63/121,200, filed on Dec. 3, 2020, the entire contents of which are hereby incorporated by reference.

BACKGROUND OF THE INVENTION

Field of the Invention

This invention relates to corneal marker tools used in ophthalmic procedures to make ink marks on the patient's cornea.

Description of Related Art

Corneal markers are used to make marks of ink or other indicator substances on the cornea of the patient's eye during ophthalmic procedures to assist in alignment of the eye with respect to the ophthalmic apparatus such as an ophthalmic laser apparatus. For example, in many laser ophthalmic procedures, the eye is engaged with the output port of the laser apparatus through a patient interface device. Some patient interfaces have a suction ring that engages the eye and a contact lens that contacts and depresses the cornea (referred to as eye docking). The docking changes the relative positional relationship between the iris and the cornea of the eye through mechanical displacement as well as optical refraction due to changes of corneal curvature. To perform laser incisions at correct locations of the eye, marks are sometimes placed on the cornea using corneal markers before the docking, so that the corneal marks can be used as a reference or a coordinate system to help transfer the location and orientation of eye features (e.g. iris pattern) before and after docking, which allows laser incisions to be placed at correct locations.

Some conventional corneal markers use a pre-inked and fully disposable single use tip configuration, where surfaces of the marking elements are pre-applied with ink. Many such corneal markers have ink coated onto the marking elements in a dry configuration, and require activation or wetting before ink can be transferred to the cornea.

Some other conventional corneal markers use a reusable and sterilizable metal stamp with a sterile ink pen or sterile stamp pad. Pen marking can be inaccurate, inconvenient and time consuming. Stamp pad inking usually requires doctors to discard the pad after a day's use as the ink pad is no longer sterile. For both of these configurations, multiple different reusable metal stamps are required in order to customize corneal marking for different patients.

SUMMARY

Accordingly, the present invention is directed to a cornea marker tool with an ink-containing applicator and consumable tips which substantially obviates one or more of the problems due to limitations and disadvantages of the related art.

An object of the present invention is to provide a more convenient and cost efficient corneal marker tool.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides a corneal marker tool assembly for ophthalmic procedures, which includes: an applicator, having a container configured to contain an ink, and a handle coupled to the container and configured to actuate the container; and a marking tip, having a base and a plurality of marking elements extending from the base, wherein the base defines a hollow interior space, wherein each of the marking elements defines a hollow interior channel in fluid communication with the hollow interior space of the base, a distal end of the hollow interior channel being either open to covered by a porous or absorbent material; wherein the base of the marking tip is configured to mate with a distal portion of the container of the applicator, and wherein the hollow interior space of the marking tip is in fluid communication with the container of the applicator when the marking tip is mated with the distal portion of the container.

In another aspect, the present invention provides a corneal marker tool for ophthalmic procedures, which includes: a marker having a plurality of marking elements; and a cap attached to the marker, the cap having an ink pad disposed within it, wherein end surfaces of the marking elements are disposed to face the ink pad with a gap in between, wherein the cap is either deformable or moveable relative to the marker to cause the ink pad to contact the end surfaces of the marking elements when the cap is deformed or moved.

In another aspect, the present invention provides a corneal marker tool for ophthalmic procedures, which includes: a marker head having a plurality of marking elements, wherein at least a distal portion of each marking elements is formed of a resin material with an ink embedded in the resin material at a distal end of the marking element; and an elongated handle joined to the marker head.

In another aspect, the present invention provides a corneal marker tool for ophthalmic procedures, which includes: a marker head having a plurality of marking elements; an elongated handle joined to the marker head; a light source embedded inside the handle; and a transparent light pipe embedded inside a distal portion of the handle and the marker head, configured to transmit a light from the light source to the marker head, wherein the marker head is configured to emit the light from a part of its surface.

In another aspect, the present invention provides a corneal marker tool for ophthalmic procedures, which includes: a marker head having a plurality of marking elements; an elongated handle joined to the marker head; and a level indicator disposed on the marker head, configured to indicate a level orientation of the marker head.

In another aspect, the present invention provides a corneal marker tool for ophthalmic procedures, which includes: a marker head having a ring shaped base and a plurality of marking elements extending from the base; and an elongated handle joined to the base of the marker head.

In another aspect, the present invention provides a corneal marker tool for ophthalmic procedures, which includes: a marker head having a base and a plurality of marking elements, wherein each marking element is an elongated prong extending from the base in a direction substantially parallel to a longitudinal axis of the marker head, wherein each elongated prong includes a thin segment that is thinner in a radial direction than segments above and below the thin segment, and wherein each marking element has a distal end that extends in a substantially radial direction and is inclined relative to a plane perpendicular to the longitudinal axis; and an elongated handle joined to the base of the marker head.

In another aspect, the present invention provides a corneal marker tool assembly for ophthalmic procedures, which includes: a corneal marker tool having a ring shaped base with a center opening and a plurality of marking elements joined to and extending from a bottom side of the base and located around the center opening; and a ring shaped nesting adapter having a center opening and a step feature within the center opening, wherein the base of the corneal marker tool is configured to fit within the center opening of the nesting adapter and rest on the step feature, with the marking elements of the marker tool exposed through the center openings of the nesting adapter.

In another aspect, the present invention provides a corneal marker tool assembly for ophthalmic procedures, which includes: an elongated handle; and a marking tip, configured to be attachable to and detachable from the handle, the marking tip including a distal portion with a plurality of marking elements; wherein a distal portion of the handle and a proximal portion of the marking tip are configured to make with each other to detachably attach the marking tip to the handle. In some embodiments, the plurality of marking elements includes a first subset of marking elements extending from a first side of the distal portion of the marking tip and a second subset of marking elements extending from a second side of the distal portion of the marking tip, the first and second subsets of marking elements having different geometries.

It is to be understood that both the foregoing general description and the following detailed description are exemplary and explanatory and are intended to provide further explanation of the invention as claimed.

BRIEF DESCRIPTION OF THE DRAWINGS

FIGS. 1A-1D illustrate a corneal marker tool including an ink-storing applicator and a disposable marking tip according to a first embodiment of the present invention.

FIGS. 2A-2E illustrate a number of different tips of the corneal marker tool of FIG. 1 according to various alternative embodiments of the present invention.

DETAILED DESCRIPTION OF PREFERRED EMBODIMENTS

Figure 3A:
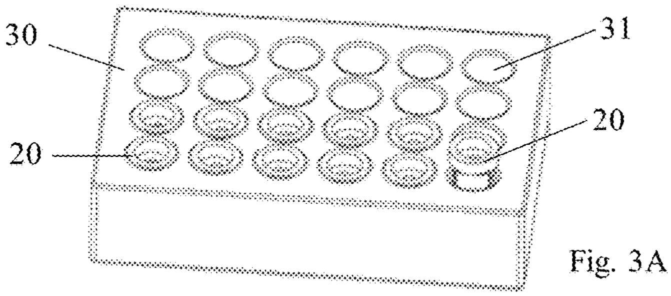
FIGS. 3A-3C illustrate a packaging of the tips of the corneal marker tool of FIG. 1 according to the first embodiment of the present invention.

A first embodiment of the present invention provides a corneal marker tool which includes an applicator and a separate consumable marking tip. The marking tip can be easily installed onto and ejected from the applicator. The applicator has a container that stores an amount of liquid ink; the ink is injected into the tip by force applied during tip installation and readily flows to the distal end of the marking elements of the tip, which readies the corneal marker for use. This combined action of installation and ink injection streamlines the workflow and facilitates fast corneal marking operation. The tip may be disposed of after a single use, while the applicator may be used repeatedly without ink re-filling.

FIGS. 1A-1D schematically illustrate a corneal marker tool according to the first embodiment, where FIGS. 1A and 1B are two side views from different directions, and FIGS. 1C and 1D are cross-sectional views viewed along the arrows C-C' in FIG. 1B.

The corneal marker tool 1 includes an applicator 10 and a marking tip 20. The applicator 10 includes a body (a sleeve) 11, a handle 12 partially disposed within and protruding from the body 11, and a container 13 disposed inside the body for containing a liquid ink (or more generally, any indicator substances that can be dispensed on the cornea to form marks). The handle 12 is mechanically connected to the container 13. The container 13 may be a separate piece disposed inside the sleeve 11, or it may be simply a chamber formed by the interior walls of the sleeve 11 and the distal end face of the handle 12 (i.e. no separate piece is required). The handle 12 engages the body 11 with a lead screw or other suitable mechanism to actuate the container 13. Once the tip 20 is attached to the distal end of the applicator 10, the lead screw or the other mechanism is used to direct a volume of liquid ink distally toward an outlet port in the tip by twisting. The handle and the body may include a biasing mechanism to provide an audible or tactile feedback (a click) of the movement of the lead screw or the other mechanism. The biasing mechanism may be, for example, one or more pieces of resilient material on the handle (or the interior of the body), and one or more small indentations or protrusions on the interior of the body (or the handle), which engage with each other when the handle is twisted.

In operation, the handle 12 may be twisted to inject the ink into the tip, and the center of the handle may be depressed to eject the tip 20. The tip 20 is preferably a single use, disposable component.

The tip 20 includes a base 21 and a number or marking elements (e.g. prongs) 22 extending from the base. The base 21 is shaped like a cap to fit over a distal end section of the applicator container 13 so as to install the tip 20 onto the applicator 10. The base 21 defines a hollow interior space 21A, and each prong 22 has a hollow interior channel 22A in fluid communication with the interior space of the base. The hollow interior channel 22A is open at the distal end of the prong to dispense ink onto the cornea. Alternatively, a porous or absorbent material may be provided at the distal end of each prong to facilitate ink transfer to the cornea. The interior spaces 21A and interior channels 22A are empty (i.e. containing no ink) before the tip is installed onto the applicator. In other words, the tip is not pre-inked. As shown in FIGS. 1C and 1D, when the tip is installed onto the applicator, the entire container 13 is depressed to "snap on" the tip, causing ink to be injected from the container into the interior spaces 21A and interior channels 22A of the tip. Alternatively or in addition, the interior spaces 21A and interior channels 22A of the tip 20 may facilitate a capillary action to allow the ink to be drawn from the container 13 into the tip, including the space 22A inside the prongs 22.

As shown in FIGS. 2A-2E, the exterior shapes of the prongs 22 of the tip 20 may have various different configurations. For example, as shown in FIGS. 2A and 2B, the angle of the prongs 22 relative to a transverse plane (a plane perpendicular to the longitudinal direction of the tip and the applicator) may have a value from about 80 degrees (i.e. the prongs lean slightly inwardly) to 90 degrees (i.e. the prongs extends straight out). The distal end surfaces of the prongs 22 may be shaped to lie on a curved surface (concave from the perspective of the tip) having a radius of curvature from about 11.0 to about 12.0 mm, as shown in FIGS. 2C and 2D. Different radius of curvature are configured to allow customization for different patients for better corneal fitment. The height of the tip 20 including the base 21 and the prong 22 may be from 16.0 mm to 17.5 mm, as shown in FIGS. 2B and 2D. As shown in FIGS. 2D and 2E, the liquid ink channels within the tip may have different sizes and different opening shapes at the distal end.

In different embodiments, the tip 20 may have different number of prongs, such as two, three, four, etc. In different embodiments, the end surfaces of the prongs 22 may have different shapes in the distal end view (viewed along the longitudinal direction). The base 21 of the different tip configurations are preferably the same.

Figure 3B:
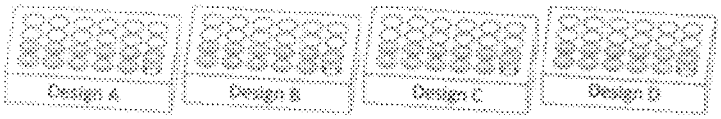
Figure 3C:
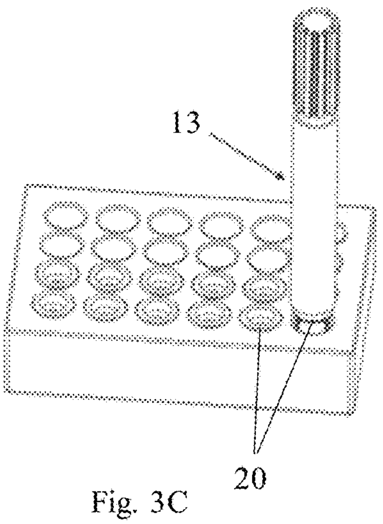

Multiple tips 20 may be packaged in a multi-welled tray, as shown in FIG. 3A, to facilitate convenient installation onto the applicator. Tips of different shapes may be packaged in different trays for convenience (see FIG. 3B). The tray 30 is preferably rectangular but may have any suitable shape. A plurality of wells 31 are formed in the tray, each accommodating a tip 20, with the base 21 facing upwards. As shown in FIG. 3C, when installing a tip 20 onto an applicator 10, the doctor inserts the distal end section of the applicator container 13 into the base 21 of a tip that is situated in the tray, and apply a force to "snap on" the tip. The force causes the ink in the container to be injected into the tip including the interior spaces of the prongs. The injection occurs automatically when the tip is installed without requiring other actions of the doctor. In alternative embodiments, the ink is not automatically injected into the tip with the tip is installed; a twisting and/or pressing of the handle is required to inject ink into the tip.

Other embodiments of corneal marker tools are described below. The marker tools in these embodiments are used without an applicator.

Figure 4A:
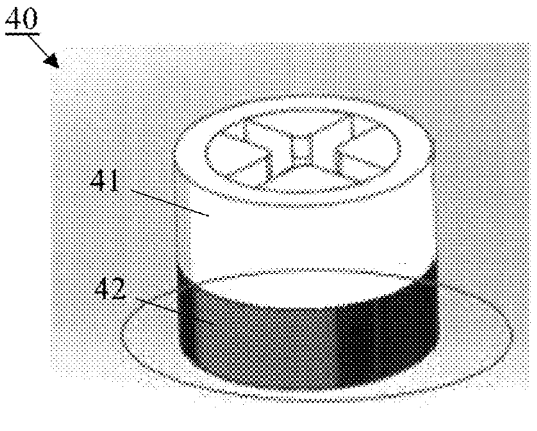
FIGS. 4A and 4B illustrate a non-inked, disposable, self-contained corneal marker tool with a single-use ink pad according to a second embodiment of the present invention.
Figure 4B:
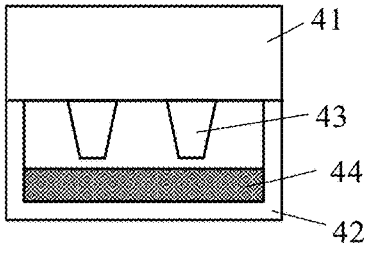

FIGS. 4A (exterior perspective view) and 4B (side cross-sectional view) illustrate a non-inked, single-use disposable, self-contained corneal marker tool with a single-use ink pad according to a second embodiment of the present invention. The corneal marker tool 40 includes a sterile, single-use marker 41 with marking elements 43 and an ink pad 44 embedded in its cap 42. The marking elements 43 are non-inked and are disposed to face the ink pad 44 with a small gap in between when the cap is normally attached to the marker 41. When the cap is manipulated by the user, e.g., depressed or twisted, the end surfaces of the marking elements come in contact with the ink pad and are wetted with ink. For example, the bottom of the cap 42 may be slightly deformable when pressed, to allow the ink pad to contact and wet the end surface of the marking elements 43. In an alternative example (not shown), the cap 42 is engaged with the marker 41 by threads, and when the cap is rotated relative to the marker, the cap and the marker move toward each other so that the ink pad 44 within the cap makes contact with the end surface of the marking elements 43. After the marking elements are inked, the cap is separated form the marker, and the marker is ready to use. The number of marking elements on the marker 41 and their shapes may have a variety of configurations, similar to the earlier-described embodiments. In one example, the marker has a cross shape that makes four marks on the cornea.

Figure 5:
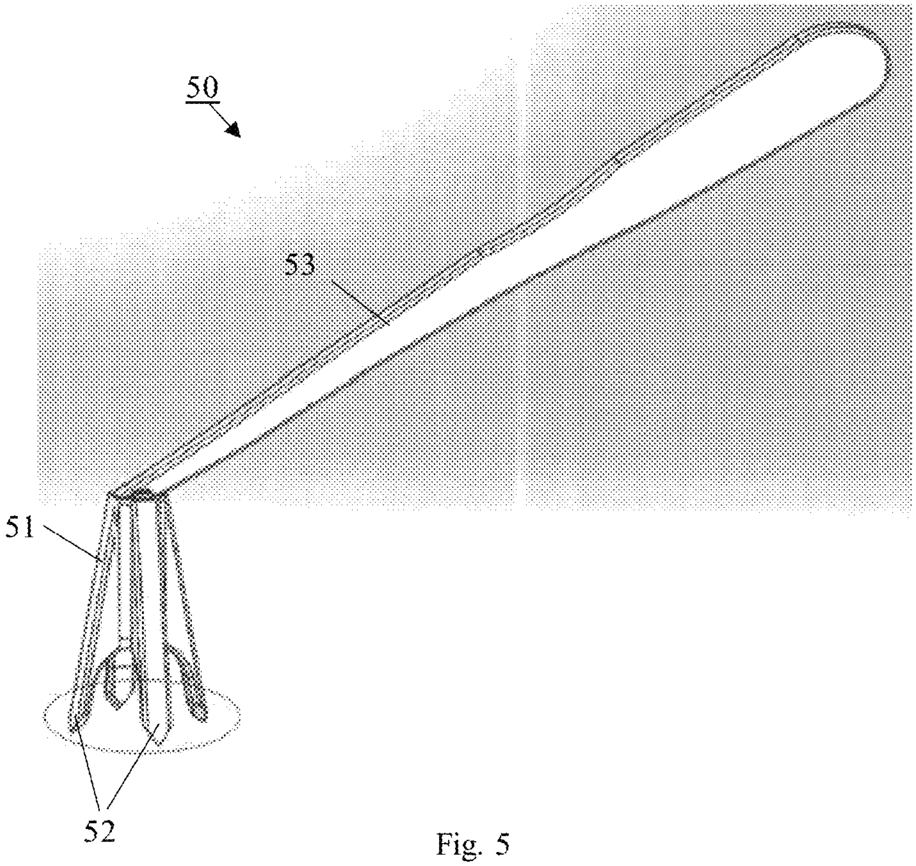
FIG. 5 illustrates a pre-inked, disposable corneal marker tool with ink-embedded marking elements according to a third embodiment of the present invention.

FIG. 5 illustrates a pre-inked, single-use disposable corneal marker tool with ink-embedded marking elements according to a third embodiment of the present invention. The corneal marker tool 50 includes a marker head 51 having a number of marking elements (e.g. prongs) 52, and an elongated handle 53 fixedly joined to the marker head to form a one-piece tool. The marker head 51, or at least the distal portions of the marking elements 52, are formed of a resin material, with an ink (or other suitable indicator substances) embedded in the resin material at the distal ends of the marking elements. This corneal marker tool may be formed by 3D printing or over-molding. The number of marking elements 52 and their shapes may have a variety of configurations, similar to the earlier-described embodiments. An advantage of this embodiment is that the manufacturing method is more streamlined as it does not require a separate step of coating the distal ends of marking elements with ink (e.g., by spraying, dipping, etc.)

Figure 6A:
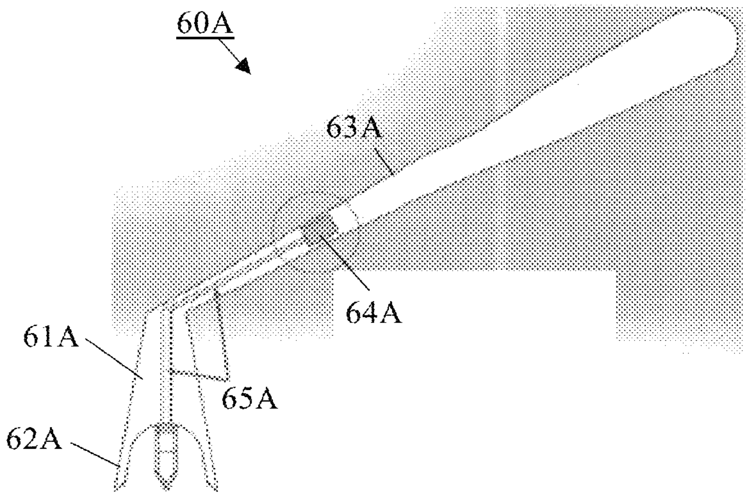
FIGS. 6A and 6B illustrate a pre-inked, disposable corneal marker tool with an illumination light according to a fourth embodiment of the present invention.
Figure 6B:
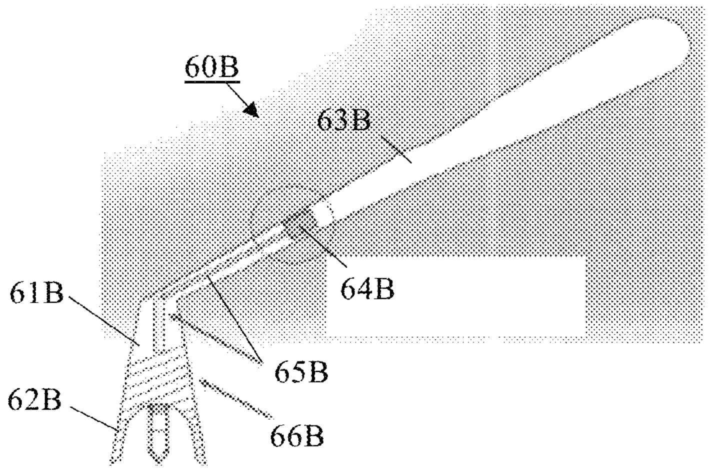

FIGS. 6A and 6B illustrate a pre-inked, single-use disposable corneal marker tool with an illumination light according to a fourth embodiment of the present invention. In one implementation of the embodiment, shown in FIG. 6A, the corneal marker tool 60A includes a marker head 61A having a number of marking elements (e.g. prongs) 62A, and an elongated handle 63A fixedly joined to the marker head to form a one-piece tool. A light source 64A (e.g., an light emitting diode (LED) with associated battery) is disposed inside the handle 63A. A transparent light pipe 65A is embedded (e.g. by molding) inside a distal portion of the handle and in the marker head 61A to transmit the light from the light source to a distal end surface of the marker head at the base of the prongs 62A. Preferably, the distal portion of the light pipe is eccentric, i.e., non-coaxial with the central axis of the marker head, so that the light provides radial illumination of the surgical field under the tool.

In an alternative of the embodiment, shown in FIG. 6B, the prongs 61B, handle 62B, light source 63B, and light pipe 64B of the corneal marker tool 60B are similar to those of the corneal marker tool 60A, but the surface of a distal section of the marker head including the prongs has a finish 65B (e.g., frost or polished) that allows the light to be more effectively emitted from these surface areas to illuminate a wider field under the tool.

In an alternative, instead of a light source 64A, an internal liquid ink storage may be provided in the handle 63A, or inside the marker head 61A; internal liquid channels may be provided inside the marker elements (prongs) 62A and connected to the ink storage to allow the end of the marker elements to be inked.

Figure 7:
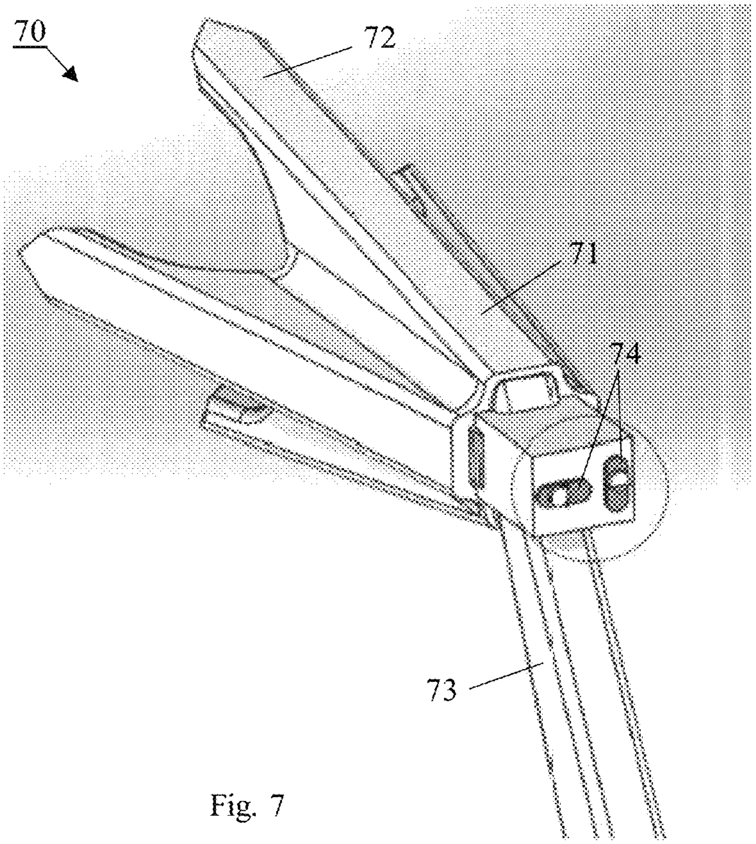
FIG. 7 illustrates a pre-inked, disposable corneal marker tool with a built-in leveling feature according to a fifth embodiment of the present invention.

FIG. 7 illustrates a single-use disposable corneal marker tool with a built-in leveling feature according to a fifth embodiment of the present invention. The corneal marker tool 70 includes a marker head 71 having a number of marking elements (e.g. prongs) 72, and an elongated handle 73 joined to the marker head to form a one-piece tool. A level indicator 74, for example one or more bubble levels (a tube containing a liquid and a gas bubble) or ball levels (a tube containing a ball), is provided on the marker head 71, for example, on a block where the handle 73 joins the marker head. The level indicator 74 may be formed on the marker head by over-molding. In the example shown in FIG. 7, two orthogonal bubble levels 74 are provided on a transverse surface of the marker head 71 (i.e. a surface perpendicular to the longitudinal axis of the marker head). Note that the longitudinal axis is the axis to be aligned with the optical axis of the eye when marking the eye; the marking elements are disposed around the longitudinal axis. The level indicator provides a visual feedback to the doctor as to the vertical and/or horizontal orientations of the corneal marker tool during marking.

Preferably, the marker head 71 is pivotally joined to the handle 73 so that the marker head can rotate around the longitudinal axis of the marker head with respect to the handle. In addition, a locking mechanism may be provided for locking the preferred orientation (the rotational angle) of the marker head with respect to the handle. The locking mechanism may be, for example, a sphere and collet, sphere and pivot, a sphere and lock, or other suitable mechanical structures.

Figure 8:
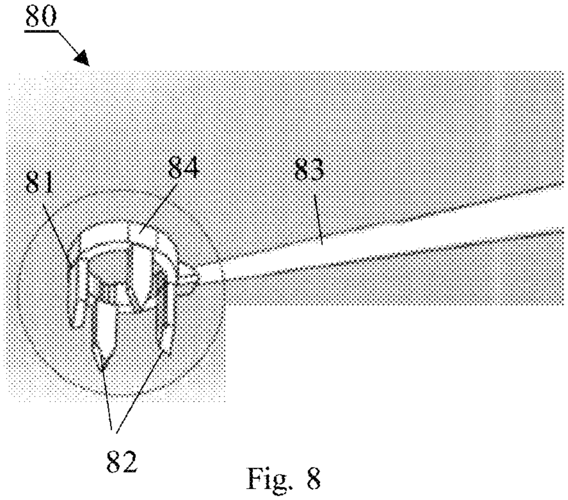
FIG. 8 illustrates a disposable corneal marker tool with a ring shaped base according to a sixth embodiment of the present invention.

FIG. 8 illustrates a single-use disposable corneal marker tool with a ring shaped base according to a sixth embodiment of the present invention. The corneal marker tool 80 includes a marker head 81 having a number of marking elements (e.g. prongs) 82, and an elongated handle 83 fixedly joined to the marker head to form a one-piece tool. The marker head 81 has a ring shaped base 84 joined to the handle 83, where the marking elements 82 are joined to and extend substantially perpendicularly from the ring. The ring shaped base 84 has a center opening, with the marking elements 82 disposed around the opening, which facilitates visualization of the eye and alignment of the tool during marking.

Figure 9:
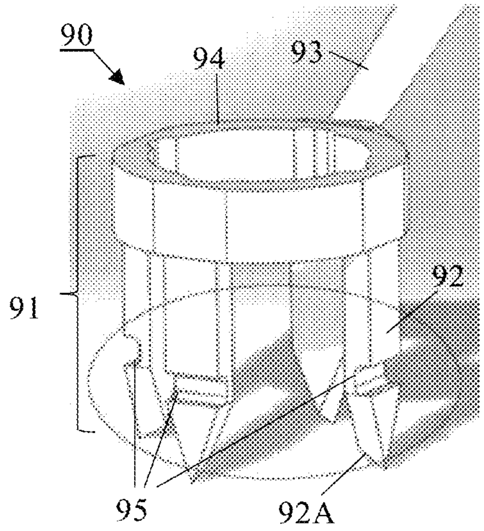
FIG. 9 illustrates a disposable corneal marker tool with leaf spring features on the marking elements according to a seventh embodiment of the present invention.

FIG. 9 illustrates a single-use disposable corneal marker tool with leaf spring features on the marking elements according to a seventh embodiment of the present invention. The corneal marker tool 90 includes a marker head 91 having a number of marking elements (e.g. prongs) 92, and an elongated handle 93 fixedly joined to the marker head to form a one-piece tool. The marker head 91 has a base 94 joined to the handle 83, where the elongated marking elements 92 are joined to and extend from the base. The marking elements extend in directions substantially parallel to a longitudinal axis of the marker head and are disposed around the axis. Each prong 92 has a leaf spring feature, which may be implemented as a cutout 95 formed in the prong to make a segment of the prong thinner in a radial direction than the segments above and below it. Here, the radial direction is a direction perpendicular to and radiating from the center axis of the marker head. In the example shown in FIG. 9, the cutout is a radially outer portion of that segment of the prong, i.e., the remaining material is a radially inner portion of the prong. In alternative embodiments, the cutout may be a radially inner portion of the segment of the prong. The cutout enables the distal segment of the prong (i.e. the segment beyond the cutout) to bend in a radial direction relative to the rest of the prong (i.e. the segment between the base and the cutout). This allows the distal ends 92A of the prongs to form a better contact with the cornea, which improves ink transfer to the cornea. As shown in FIG. 9, the distal end 92A of each prong is oriented in a substantially radial direction, and is inclined relative to the transverse plane (i.e. a plane perpendicular to the longitudinal direction of the marker head) to accommodate the curvature of the cornea. The amount of the spring force of the leaf spring feature may be controlled by changing the dimension of the cutouts. More generally, the geometry of the end surface of the prongs, the amount of ink coated on the end surface, and the spring geometry are variables that affect the geometry of the resulting corneal ink mark and may be designed based on practical needs.

It should be noted that although in the embodiment illustrated in FIG. 9, the base 94 of the marker head 91 has a ring shape similar to the embodiment of FIG. 8, this is not required. The leaf spring feature may be implemented in any of the earlier described embodiments that have elongated marking elements (prongs).

Figure 10A:
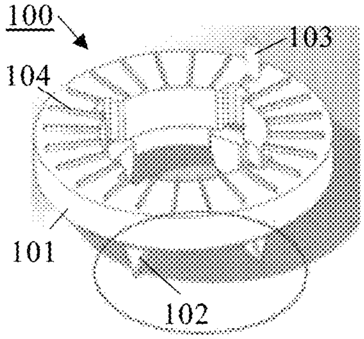
FIGS. 10A-10E illustrate a disposable corneal marker tool configured to nest within a patient interface according to an eighth embodiment of the present invention.
Figure 10B:
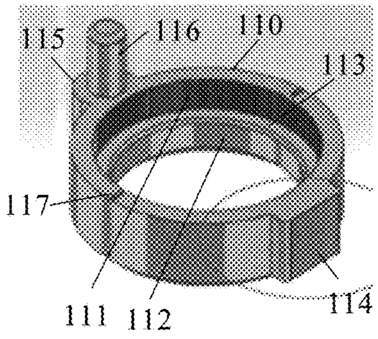
Figure 10C:
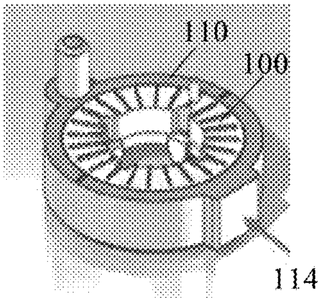
Figure 10D:
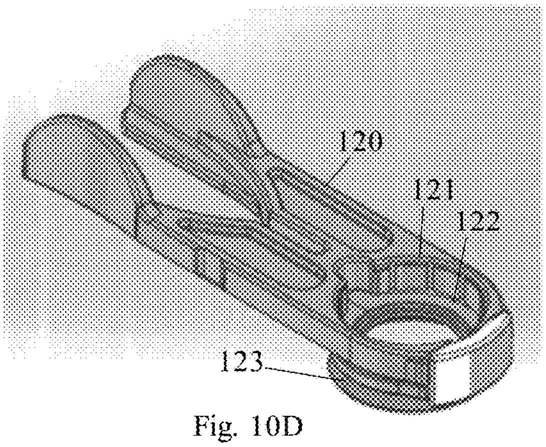
Figure 10E:
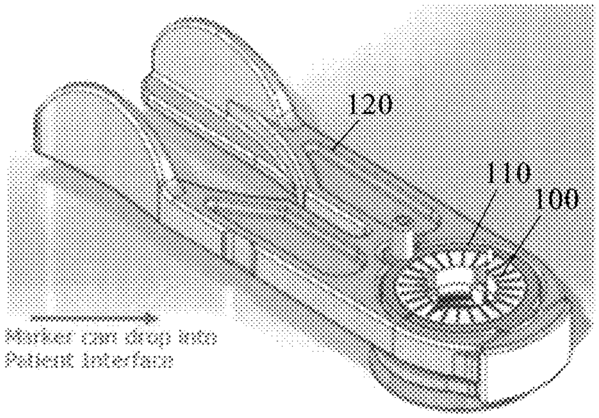

FIGS. 10A-10D illustrate a single-use disposable corneal marker tool configured to nest within a patient interface according to an eighth embodiment of the present invention. As shown in FIG. 10A, the corneal marker tool 100 has a ring shaped base (dial) 101 and a number of marking elements (e.g. prongs) 102 which are joined to and extend downwardly and substantially perpendicularly from the bottom side of the base around the center opening of the base. A ring shaped nesting adapter 110 having a center opening is also provided in this embodiment (FIG. 10B); the marker tool 100 fits within the nesting adapter 110 (FIG. 10C), and the adapter with the marker tool may then be mounted in the patient interface component 120 (FIGS. 10D and 10E). In this embodiment, the marker tool 100 is a disposable element, while the nesting adapter 110 and the patient interface component 120 are re-useable.

More specifically, as shown in FIG. 10B, the ring shaped nesting adapter 110 has an upper section 111 with a larger inner diameter than that of a lower section 112, forming a step feature 113 inside the ring. The base 101 of the marker tool 100 has an outer diameter approximately equal to the inner diameter of the upper section 111 of the adapter and is configured to rests on the step feature 113. As shown in FIG. 10D, the patient interface component 120 is a gripper having an open port 121 with a step feature 122 inside, allowing the nesting adapter 110 to be fitted inside the port and rest on the step feature. A flexible suction ring 123 with a vacuum port (not shown) is attached to the lower side of the patient interface component 120 and located coaxially with the open port 121, configured to attach the patient interface component 120 to the patient's eye by vacuum force. Note that the patient interface component 120 is a gripper component of a patient interface assembly that also includes other components; the open port of the gripper is designed to receive a lens cone component of the patient interface assembly. Further description of the entire patient interface may be found in commonly owned U.S. Pat. Appl. Pub. No. 2002/0103481.

When the marker tool 100 is nested inside the adapter 110 and the adapter is nested inside the patient interface component 120, the center openings of the marker tool, the nesting adapter, the port 121 of the patient interface component and the suction ring 123 are all coaxially aligned to allow visualization of the eye while marking. Moreover, in the nested configuration, the marking elements 102 of the marker tool 100 are exposed through the center openings of the adapter 110, the port of the patient interface component 120 and the suction ring, allowing them to contact the cornea when the patient interface component 120 is attached to the patient's eye via the suction ring 123. Having the patient interface component 120 attached to the eye when marking provides more stability and improves marking result.

When installed in the patient interface component 120, the marker tool 100 may be rotated within the nesting adapter to change the orientation of the marker tool. A post 103 may be provided on the marker tool 100, extending upwardly from the top side of the base 101, to facilitate easy handling of the tool and/or to serve as an orientation indicator. Additional orientation indicators (e.g. radial lines 104) may be provided on the top surface of the marker tool to help with alignment. For this purpose, the top side of the nesting adapter 110 also includes orientation indicators (e.g. radial lines 117) that may be aligned with the lines 104 of the marker tool. The outer shape of the nesting adapter 110 has one or more asymmetrical features 114, 115 which mate with the shape of the open port 121 of the patient interface component 120, which serves to fix the orientation of the nesting adapter relative to the patient interface component (see FIGS. 10B, 10D, 10E). The nesting adapter 110 further includes a post 16 for easy handling of the adapter.

This corneal marker tool offers improved alignment with the patient's limbus and can be rotated to align with meridians and axes of the eye. The tool is adaptable to utilize patient interface suction to attach to eye and provide stability while marking.

Figure 11A:
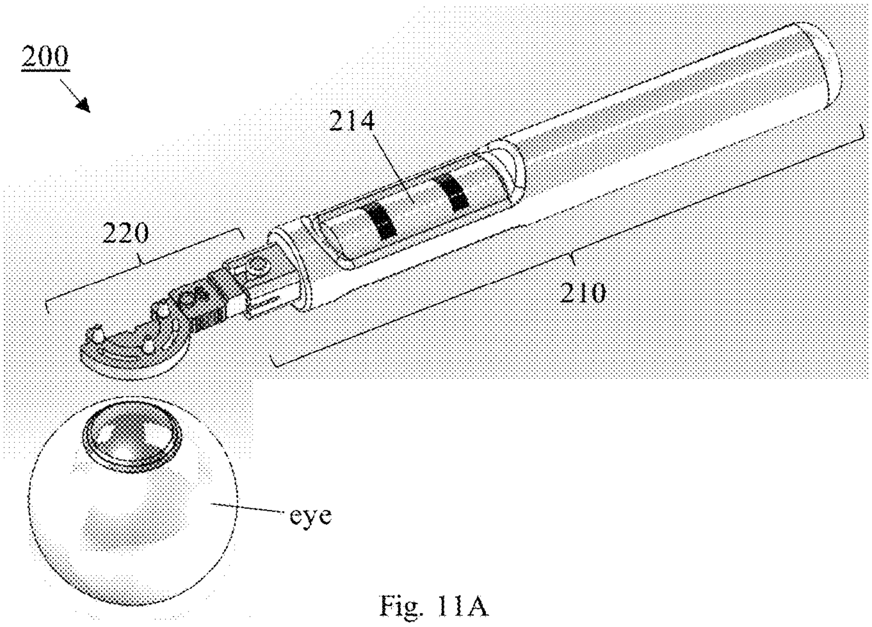
FIGS. 11A-11E illustrate a corneal marker tool having a reusable handle and a pre-inked, disposable marking tip according to a nineth embodiment of the present invention.
Figure 11B:
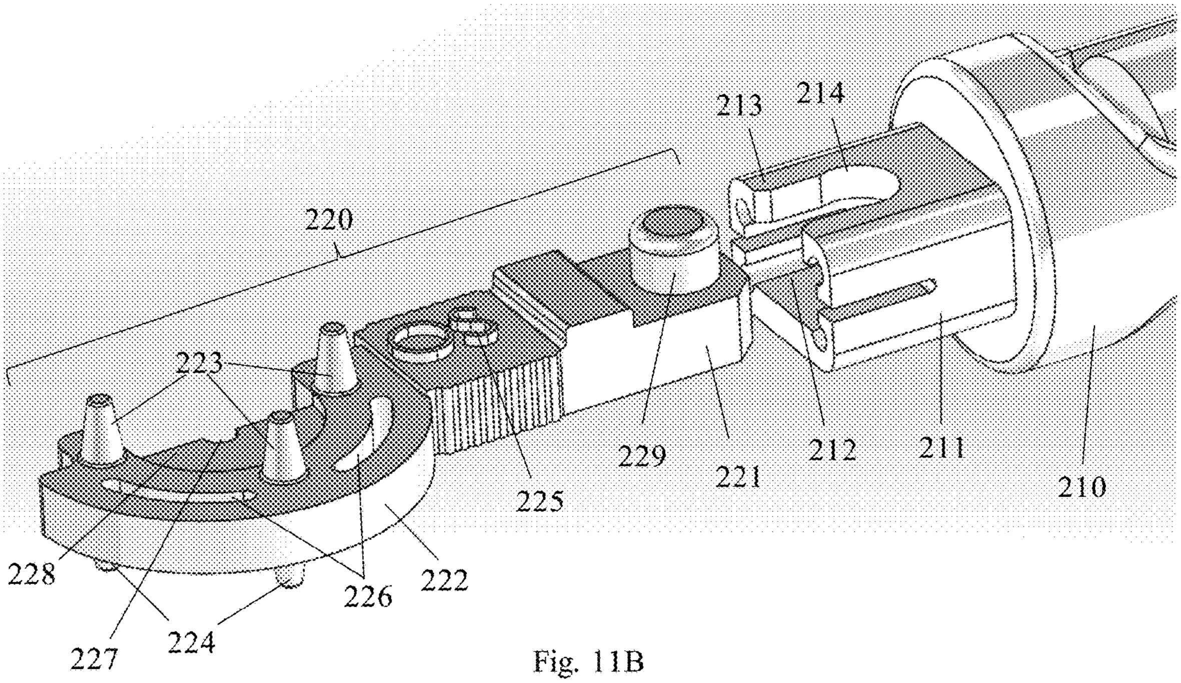
Figure 11C:
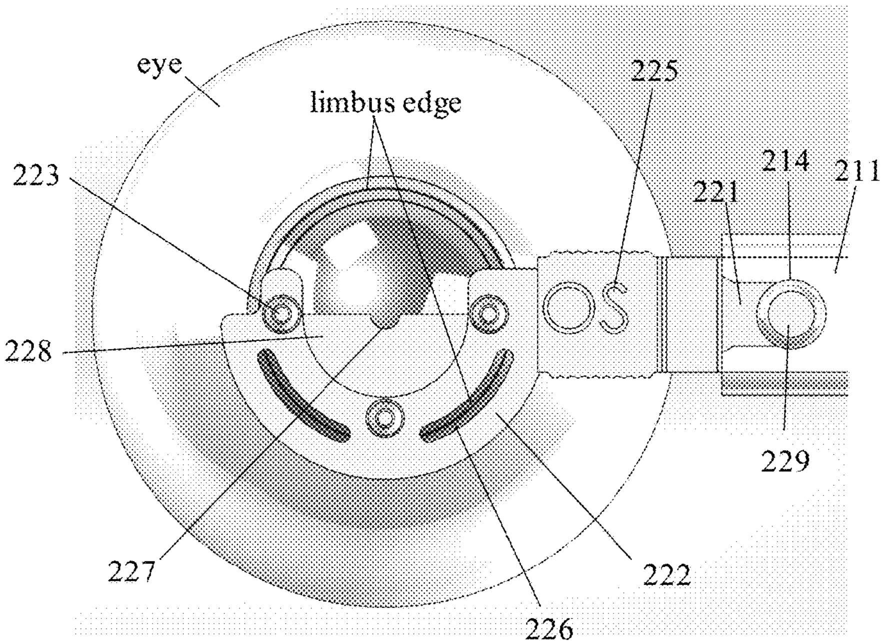

FIGS. 11A-11E illustrate a corneal marker tool that includes a reusable handle and a pre-inked, disposable marking tip according to a nineth embodiment of the present invention. The marking tip 220 is attached to the distal end of the elongated handle 210 for use as a marker tool, and detached from the handle and discarded afterwards. FIGS. 11A and 11B (perspective views) show the tip 220 attached to the handle 210 and detached from the handle, respectively. FIG. 11C (top view) illustrates the tip 220 overlaid on the eye.

A proximal portion 221 of the tip 220 and a distal portion 211 of the handle 210 have shapes that mate with each other to attach the tip to the handle. In the illustrated embodiment, the distal portion 211 of the handle forms a slot 212, and the proximal portion 221 of the tip is shaped to fit inside the slot. Preferably, the distal portion 211 of the handle 210 includes resilient members 213 that form the slot 212, where the resilient members are slightly deformed when the proximal portion 221 of the tip is inserted in the slot, to form a tight fit and to effectively retain the tip 220 on the handle 210. The proximal portion 221 of the tip 220 and the distal portion 211 of the handle 210 may have additional retention features that cooperate with each other to retain the tip on the handle. For example, in the illustrated embodiment, the proximal portion 221 of the tip 220 has a protruding round button 229, and the resilient member 213 has a keyhole shaped slot 214, to create a snap lock that securely retains the tip 220 on the handle 210 when the button 229 is moved into the wider part of the keyhole. In the illustrated embodiment, the button 229 is disposed on only one side of the proximal portion 221 of the tip, and the distal portion 211 of the handle has only one keyhole shaped slot, so that the button and keyhole slot can serve as an orientation lock to ensure that the tip can only be attached to the handle in one orientation.

Other suitable structures may be used for the proximal portion 221 of the tip and the distal portion 221 of the handle for the purpose of attaching and securing the tip to the handle. For example, the proximal portion 221 of the tip may form a slot and the distal portion 211 of the handle may be shaped to fit inside the slot.

The tip 220 defines a center axis (perpendicular to the drawing sheet in FIG. 11C), which is to be aligned approximately with the optical axis of the eye when marking the eye. A distal portion 222 of the tip extends transvers to the axial direction, and a plurality of marking elements (e.g. prongs) 223 and 224 extend from the distal portion in directions substantially parallel to the center axis. The marking elements, which have pre-inked end surfaces, include a first plurality of (e.g., 3) marking elements 223 on one side of the distal portion 222 and a second plurality of (e.g., 3) marking elements 224 on the other side. The marking elements 223 and 224 on different sides of the tip preferably have different geometries (e.g. angles of the end surfaces of the marking elements) that are configured and optimized for marking right and left eye corneas, respectively. Corresponding insignias 225 may be provided on the respective sides of the tip 220 to conveniently indicate the left- or right-eye-marking orientation of the tool. For example, in the illustrated embodiment, the upward-facing insignia "OS" indicates that the marking elements 224 on the other side of the tip are for marking the left eye.

A number of arcuate windows 226 are provided on the distal portion 222 of the tip for aligning with limbus edge of the eye when marking. The arcuate windows 226 are arcuate with respect to the center axis, and are located at a radius that approximately equals the radius of the limbus of an average eye. Further, a center notch 227 is provided at the center of the distal portion 222 to facilitate alignment with the pupil when marking the eye. The piece of material 228 at the center of the distal portion 222 that define the notch 227 preferably has a transparent, polished molding surface to facilitate viewing of eye landmarks when marking. In alternative embodiments, the distal portion 222 of the tip may be entirely made of a transparent material with circular indicator lines that indicate the positions of the pupil and limbus. In the embodiment illustrated in FIGS. 11A-C, the outline shape of distal portion 222 of the tip is approximately a half of a round disk, but it may alternatively be a full round disk.

Preferably, a built-in leveling feature 214, such as one or more bubble levels or ball levels, is provided in the handle for accurate mark placement. In the illustrated embodiment, the handle 210 extends in a longitudinal direction of the tool that is perpendicular to the axial direction of the tip 220, so when the handle is level, the distal portion 222 of the tip is level. In alternative embodiments, the handle 210 may extend in a direction that is not perpendicular to the axial direction of the tip, in which case the leveling feature is provided in a proper orientation such that it serves to indicate whether the distal portion 222 of the tip is level.

Figure 11D:
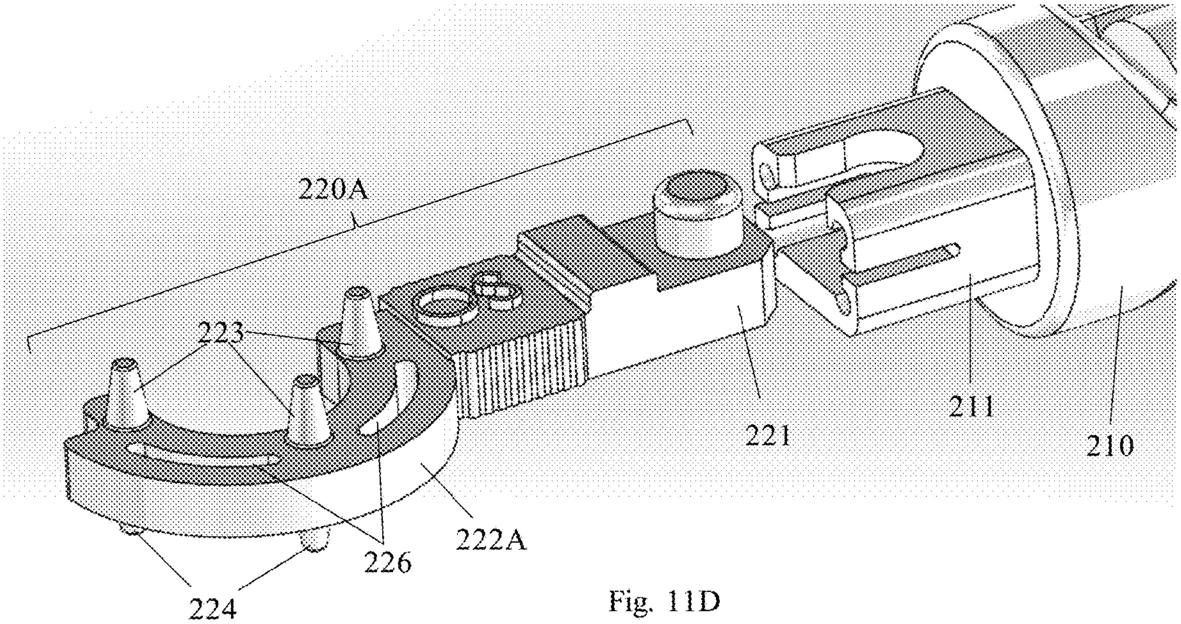
Figure 11E:
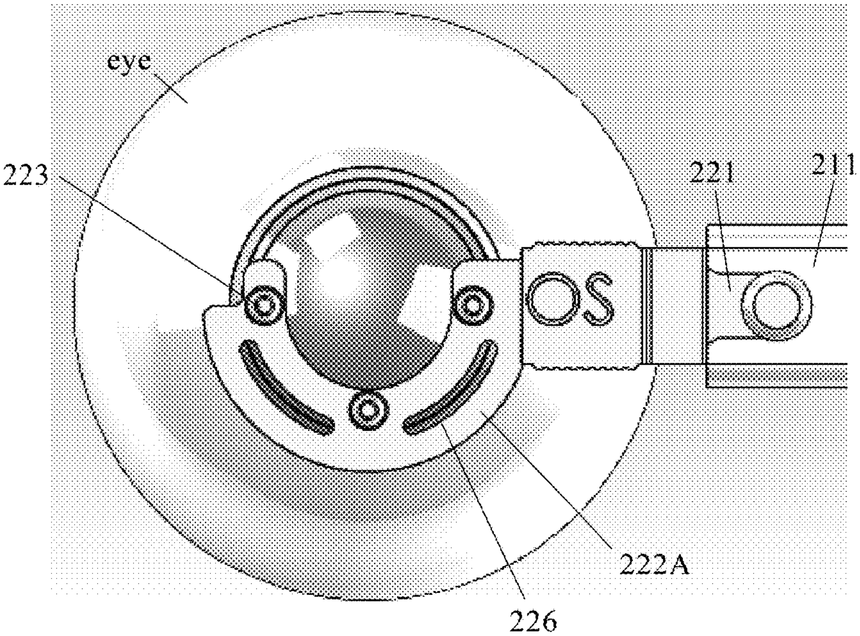

FIGS. 11D (perspective view) and 11E (top view) illustrate an alternative embodiment of a corneal marker tool that includes a reusable handle and a pre-inked, disposable tip. The alternative embodiment is similar to the embodiment shown in FIGS. 11A-11C, except that the distal portion 222A of the tip 220A does not include the piece of material 228 that defines a center notch 227.

The marking elements of any of the embodiments shown in FIGS. 5, 6A-B, 7, 8, 9, 10A-E and 11A-E may be pre-inked, for example, by coating an ink on the marker elements, or by embedding an ink in the material that forms the marker elements, or by providing internal liquid channels within the marking elements connected to a liquid ink storage within in the handle or marker head or base. Alternatively, the marking elements may be non pre-inked.

The corneal marker tools according to various embodiments of the present invention may be used in a variety of ophthalmic procedures including refractive corneal lenticular extraction, LASIK (laser-assisted in situ keratomileusis) lamellar flap realignment (i.e. replacement of the flap after refractive correction), IOL (intra-ocular lens) landmark placement (i.e. meridian marking), etc.

It will be apparent to those skilled in the art that various modification and variations can be made in the corneal marker tools of the present invention without departing from the spirit or scope of the invention. Thus, it is intended that the present invention cover modifications and variations that come within the scope of the appended claims and their equivalents.

What is claimed is:

1. A corneal marker tool assembly for ophthalmic procedures, comprising:

an applicator, having a container configured to contain an ink, and a handle coupled to the container and configured to actuate the container; and a marking tip, having a base and a plurality of marking elements extending along a longitudinal direction from the base, wherein at a defined longitudinal position, each marking element has a first width in a first side view viewed along a first transverse direction which is perpendicular to the longitudinal direction and a second width in a second side view viewed along a second transverse direction which is perpendicular to the longitudinal direction and different from the first transverse direction, the first width being larger than the second width, wherein the base defines a hollow interior space, wherein each of the marking elements defines a hollow interior channel in fluid communication with the hollow interior space of the base, a distal end of the hollow interior channel of each of the marking elements being either open or covered by a porous or absorbent material;

wherein the base of the marking tip is configured to mate with a distal portion of the container of the applicator, and wherein the hollow interior space of the marking tip is in fluid communication with the container of the applicator when the marking tip is mated with the distal portion of the container.

2. The corneal marker tool assembly of claim 1, wherein the applicator further includes a sleeve, and wherein the container is a separate piece disposed inside the sleeve.

3. The corneal marker tool assembly of claim 1, wherein the applicator further includes a sleeve, and wherein the container is a chamber formed by interior walls of the sleeve and a distal end face of the handle.

4. The corneal marker tool assembly of claim 1, wherein the applicator further includes a sleeve, and wherein the handle is partially disposed within and protrudes from the sleeve.

5. The corneal marker tool assembly of claim 1, wherein the marking elements are prongs extending from the base, wherein the prongs are angled inwardly toward a center axis of the applicator by less than 10 degrees.

6. The corneal marker tool assembly of claim 1, wherein the marking elements are prongs extending from the base, and distal end surfaces of the prongs are shaped to lie on a curved surface having a radius of curvature from 11.0 to 12.0 mm.

7. The corneal marker tool assembly of claim 1, wherein a height of the marking tip 20 including the base and the marking elements is from 16.0 mm to 17.5 mm.

8. The corneal marker tool assembly of claim 1, wherein the marking tip has two, three, or four marking elements.

9. The corneal marker tool assembly of claim 1, wherein the marking tip is configured to be attachable to and detachable from the applicator.

10. A corneal marker tool assembly for ophthalmic procedures, comprising:

an applicator, having a container configured to contain an ink, and a handle coupled to the container and configured to actuate the container; and a marking tip, having a base and a plurality of prongs extending from the base, wherein distal end surfaces of all of the prongs are shaped to lie on a common curved surface having a radius of curvature from 11.0 to 12.0 mm, wherein the base defines a hollow interior space, wherein each of the prongs defines a hollow interior channel in fluid communication with the hollow interior space of the base, a distal end of the hollow interior channel of each of the prongs being either open or covered by a porous or absorbent material, wherein the base of the marking tip is configured to mate with a distal portion of the container of the applicator, and wherein the hollow interior space of the marking tip is in fluid communication with the container of the applicator when the marking tip is mated with the distal portion of the container.

11. The corneal marker tool assembly of claim 10, wherein the applicator further includes a sleeve, and wherein the container is a separate piece disposed inside the sleeve.

12. The corneal marker tool assembly of claim 10, wherein the applicator further includes a sleeve, and wherein the container is a chamber formed by interior walls of the sleeve and a distal end face of the handle.

13. The corneal marker tool assembly of claim 10, wherein the applicator further includes a sleeve, and wherein the handle is partially disposed within and protrudes from the sleeve.

14. The corneal marker tool assembly of claim 10, wherein the prongs are angled inwardly toward a center axis of the applicator by less than 10 degrees.

15. The corneal marker tool assembly of claim 10, wherein a height of the marking tip 20 including the base and the prongs is from 16.0 mm to 17.5 mm.

16. The corneal marker tool assembly of claim 10, wherein the marking tip has two, three, or four prongs.

17. The corneal marker tool assembly of claim 10, wherein the marking tip is configured to be attachable to and detachable from the applicator.

* * * * *